US005591200A

United States Patent [19]

Cone et al.

[11] Patent Number: 5,591,200

[45] Date of Patent: Jan. 7, 1997

[54] METHOD AND APPARATUS FOR APPLYING PRESSURE TO A BODY LIMB FOR TREATING EDEMA

[75] Inventors: Alan C. Cone, Encinitas; Ralph A. Loh; Stuart A. Tenenbaum, both of San Diego, all of Calif.

[73] Assignee: World, Inc., Reno, Nev.

[21] Appl. No.: 261,684

[22] Filed: Jun. 17, 1994

[51] Int. Cl.[6] .................................................. A61B 17/00

[52] U.S. Cl. .................................................. 606/201; 601/152

[58] Field of Search .................................................. 606/201; 601/150, 601/151, 148, 149; 128/DIG. 20; 602/13

[56] References Cited

U.S. PATENT DOCUMENTS

| | | | |
|---|---|---|---|
| 1,608,239 | 11/1926 | Rosett . | |
| 2,533,504 | 12/1950 | Poor | 128/24 |
| 2,781,041 | 2/1957 | Weinberg | 128/60 |
| 3,469,602 | 9/1969 | Wiley | 137/624.2 |
| 3,659,593 | 5/1972 | Vall | 128/64 |
| 3,862,629 | 1/1975 | Rotta | 128/24 R |
| 3,866,604 | 2/1975 | Curless et al. | 128/64 |
| 4,013,069 | 3/1977 | Hasty | 128/24 R |
| 4,066,084 | 1/1978 | Tillander | 128/327 |
| 4,156,425 | 5/1979 | Arkans | 128/24 R |
| 4,202,325 | 5/1980 | Villari et al. | 128/24 R |
| 4,338,923 | 7/1982 | Gelfer et al. | 128/24 R |
| 4,408,599 | 10/1983 | Mummert | 601/152 |
| 5,014,681 | 5/1991 | Neeman | 601/152 |
| 5,031,604 | 7/1991 | Dye | 601/152 |
| 5,186,163 | 2/1993 | Dye | 601/152 |
| 5,437,610 | 8/1995 | Cariapa | 601/152 |

FOREIGN PATENT DOCUMENTS

| | | |
|---|---|---|
| 1175948 | 6/1957 | France . |
| 7335605 | 6/1957 | France . |

*Primary Examiner*—Michael A. Brown
*Attorney, Agent, or Firm*—John L. Rogitz

[57] ABSTRACT

An apparatus for treating edema by applying pressure to a patient's limb includes a sleeve that is surroundingly engageable with the limb, and the sleeve includes a plurality of flexible open-ended cells for holding respective individually inflatable replaceable bladders. Also, a fluid pump is in fluid communication with each of the bladders. The apparatus also includes a plurality of electrically-operated bladder valves, and each valve is disposed between the pump and a respective one of the bladders for selectively establishing a respective pathway for fluid communication between the pump and the associated bladder. A computer individually controls each valve to variably pressurize the bladders in a variable sequence. The computer also includes means for determining the girth of the limb being treated, and to periodically monitor the apparatus for fluid leaks.

22 Claims, 8 Drawing Sheets

SAFETY INTERLOCK

PUMPING SEQUENCE EXHAUST

METHOD AND APPARATUS FOR APPLYING PRESSURE TO A BODY LIMB FOR TREATING EDEMA

FIELD OF THE INVENTION

The present invention relates generally to methods and apparatus for applying pressure to a body limb, and more particularly to methods and apparatus for treating edema with pressure therapy.

BACKGROUND

Pooling of fluid in a patient's limbs and consequent swelling of the limb or limbs is a deleterious condition which can arise from a variety of causations. For example, patients who are bedridden for prolonged periods may experience pooling of fluid in their limbs. As another example, congenital or secondary lymphedema, i.e., stasis of lymphatic fluid in an extremity of a patient, causes painful, unsightly, and ultimately dangerous swelling of the afflicted limb.

It has been recognized that swelling of limbs can be treated by applying pressure to the limb to force static fluid in the limb toward the trunk of the patient's body. For example, U.S. Pat. No. 4,762,121 ("the '121 patent") discloses a massaging sleeve that is formed with a plurality of transversely oriented cells, and an inflatable fluid bag is disposed in each of the cells. Each fluid bag includes a fluid line connector that extends through a hole formed in the associated cell, and the fluid line connectors can be connected to respective fluid lines. To treat the patient, the sleeve is wrapped around a patient's limb, and the fluid bags are then filled with fluid to compress the limb and force fluid out of the limb toward the trunk of the body.

While effective for its intended purpose, the device disclosed in the '121 patent suffers from several inherent drawbacks. For instance, to facilitate removing a damaged bag and positioning a new bag in the cell, one side edge of each cell is open, but as recognized by the present invention it can be cumbersome and difficult to install a replacement fluid bag in a cell having only one open side edge. Another drawback to the '121 device is that the fluid line connectors extend outside the sleeve, and consequently can be unintentionally disengaged from their respective fluid lines by the patient during therapy. The present invention recognizes that a compression sleeve can be provided which overcomes both of these prior art problems.

In addition to particular compression sleeve designs, prior art devices have also included various apparatus for inflating a compression sleeve. Representative of such devices is the apparatus disclosed in U.S. Pat. No. 4,013,069 ("the '069 patent") for a sequential intermittent compression device for use in an operating room. As disclosed in the '069 patent, a pump pressurizes several fluid lines which lead to respective cells in a compression sleeve. Orifices are installed in the lines to control the rate of pressure increase in each cell (or group of cells), and the time periods between inflation of adjacent groups of cells is adjustably controlled by means of a pneumatically-operated timer. Indeed, because the '069 patented apparatus is intended for use in an operating room, it teaches the use of pneumatically-operated control components, to avoid potential sparking which could arise, according to the '069 patent, from the use of electrically-operated control components.

Furthermore, the apparatus disclosed in the '069 patent purportedly can pressurize each group of cells to a pressure that can be different from the pressure of the other cell groups, thereby establishing a pressure gradient along the limb being treated. As disclosed in the '069 patent, however, all cells are ultimately in fluid communication with each other during the inflation cycle. Consequently, while the rate of pressurization of the various cell groups can be individually established by selecting appropriately sized orifices, it is unclear that the final pressures in each group can in fact differ from each other, given that the final pressure in each cell group must eventually equalize with the pressures in the other cell groups.

Additionally, while the '069 patent discloses a means for establishing a pressure rise time for each cell group which is different from the pressure rise times of the other cell groups, the rise time of each cell group cannot be dynamically controlled. Instead, to vary the pressure rise time of a group of cells, the orifice leading to the particular cell group must be removed and replaced with a differently-sized orifice. Such a procedure is time-consuming and cumbersome, and ordinarily must be performed by a trained technician.

Further, the final pressure in each cell group of the '069 patented apparatus cannot be varied or dynamically established. Moreover, while it is possible to vary the time between filling of successive cell groups, the inflation sequence itself cannot be dynamically varied.

Thus, as a practical matter, the apparatus disclosed in the '069 patent, like other prior art devices, offers a relatively limited number of therapy options. As recognized by the present invention, however, it is desirable that a compression therapy apparatus provide a large number of therapy options to ensure the availability of a compression therapy program which is tailored to the needs and peculiar physiological requirements of the particular patient being treated. Further, the present invention recognizes that it would be advantageous to provide a means for easily and dynamically establishing the variables of a particular therapy program, as dictated by physiological changes in the patient.

Accordingly, it is an object of the present invention to provide an apparatus and method for compression therapy which can undertake a variety of compression therapy programs. Another object of the present invention is to provide an apparatus and method for compression therapy that provides for dynamically controlling the parameters of the compression therapy. Still another object of the present invention is to provide a compression sleeve for treating edema-induced swelling of a patient's limb which is easy to use and cost-effective to maintain and manufacture.

SUMMARY OF THE INVENTION

An apparatus for applying pressure to a patient's limb includes a source of pressure and a sleeve that is surroundingly engageable with the limb, and the sleeve includes a plurality of individually inflatable bladders. A plurality of electrically-operated bladder valves are in fluid communication with the source of pressure, and each bladder valve also is in fluid communication with a respective one of the bladders for selectively establishing a respective pathway for fluid communication between the source of pressure and the associated bladder. Also, a computer individually controls each valve to variably pressurize the bladders in a variable sequence.

In a preferred embodiment, a valve manifold is in fluid communication with each of the bladder valves, and an electrically-operated fill valve is in fluid communication with the source of pressure and the valve manifold for selectively establishing fluid communication between the source of pressure and the valve manifold. Additionally, an electrically-operated exhaust valve is in fluid communication with the valve manifold for selectively depressurizing the valve manifold. Preferably, the fill valve and the exhaust valve are controlled by the computer.

Furthermore, a pressure sensor is preferably in fluid communication with the manifold for generating an electrical pressure signal representative of the pressure within the valve manifold. As intended by the present invention, the pressure sensor is electrically connected to the computer for sending the pressure signal to the computer. Accordingly, the computer includes a tester for determining the fluid integrity of each bladder in response to the pressure signal. Also, the computer includes an interlock for preventing pressurizing a bladder upon the occurrence of a predetermined condition. In one presently preferred embodiment, the interlock prevents pressurizing a first bladder to a greater pressure than the pressure of a second bladder distal to the first.

Additionally, a timer measures the time period for filling at least one bladder, and the timer generates a timing signal in response thereto. Each bladder defines an annular ring when the sleeve is operably engaged with a limb, and the computer includes a determiner for determining the radius of at least one of the rings based on the timing signal.

In another aspect of the present invention a method is disclosed for treating a body limb by applying pressure to the limb using a sleeve having a plurality of successively overlapping inflatable bladders extending proximally to distally along the sleeve. The method includes the steps of engaging the sleeve with the body limb in a surrounding relationship therewith, and then directing fluid into the distal-most bladder to establish a first predetermined dynamically variable pressure within the distal-most bladder for a first dynamically variable time period. Also, the method includes directing fluid into a first proximal bladder which is adjacent the distal-most bladder to establish a second dynamically variable pressure within the first proximal bladder for a second dynamically variable time period. The first pressure in the distal-most bladder is established such that when the first proximal bladder is pressurized, the first pressure in the distal-most bladder increases to a predetermined pressure. The first and second pressures are maintained for respective first and second hold periods.

In yet another aspect of the present invention, a method for treating edema includes the steps of positioning a sleeve including a plurality of inflatable bladders against a body limb in a surrounding relationship therewith, and then directing fluid into at least one bladder to compress the limb an urge fluid in the limb away from the area of compression. Then, the bladder is isolated to hold the fluid in the bladder. Next, at least one of: fluid pressure within the bladder and the time period during which fluid was directed into the bladder is measured. A girth of the limb is determined based upon at least one of: the time period and the fluid pressure.

In still another aspect of the present invention, a sleeve which is positionable around a body limb for treating edema in the limb includes first and second layers, with each layer being formed with a distal end, a proximal end, and first and second sides extending longitudinally between the ends to respectively establish a distal end of the sleeve, a proximal end of the sleeve, and first and second sides of the sleeve. Also, the sleeve includes a plurality of cell pockets extending transversely from side to side to establish a plurality of flexible cells. A plurality of inflatable bladders are positioned in a respective cell. In accordance with the present invention, each cell has respective first and second ends juxtaposed with the first and second sides, respectively, of the layers of the sleeve, and both ends of each cell are open to facilitate replacing the associated bladder with another bladder.

In another aspect of the present invention, a sleeve is positionable around a body limb for treating edema in the limb, and the sleeve includes a plurality of cells which establish a surface. A plurality of inflatable bladders are positioned, each in a respective cell, and at least one first fastening strip is attached to the surface and at least one second fastening strip configured for engaging the first fastening strip. As intended by the present invention, the second fastening strip is removably attached to the surface for permitting easy replacement of the second fastening strip with another like strip without tearing or cutting the surface.

In yet another aspect of the present invention, an apparatus is disclosed for inflating a sleeve that has a plurality of inflatable bladders. The sleeve is inflated when the sleeve is surroundingly engaged with a body limb for compressing the limb, and the apparatus includes a fluid pump and a plurality of fluid pathways in fluid communication with the fluid pump, with each fluid pathway connecting the fluid pump to a respective one of the bladders. A plurality of valves, each being disposed in a respective one of the fluid pathways, selectively establish fluid communication from the fluid pump to the associated bladder. Each valve is controllable independently of the other valves to dynamically establish a sequence of filling the bladders and to dynamically establish the pressure within each bladder independently of the pressures in the other bladders.

The details of the present invention, both as to its structure and operation, can best be understood with reference to the accompanying drawings, in which like reference numerals refer to like parts, and in which:

DETAILED DESCRIPTION OF THE PREFERRED EMBODIMENT

Figure 1:
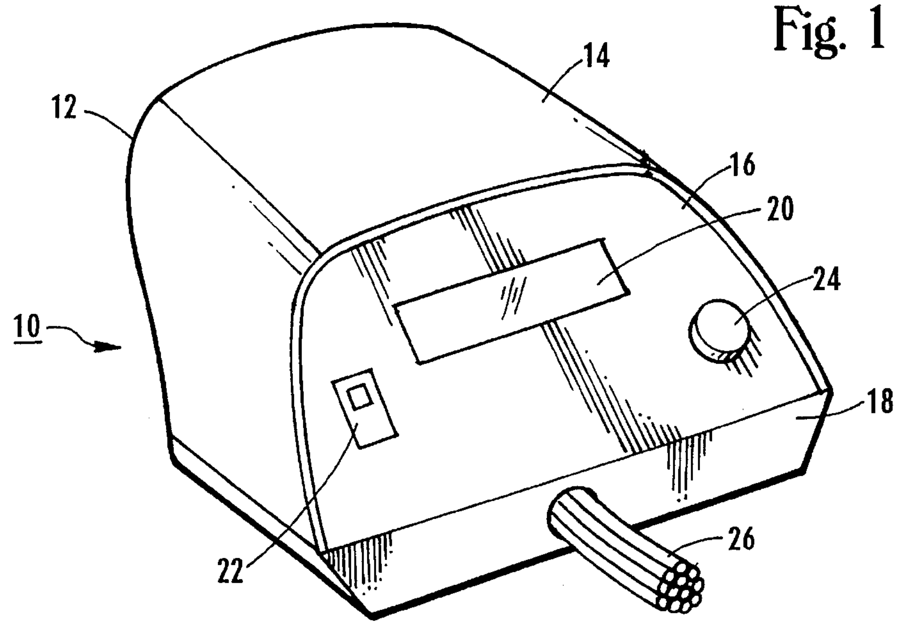
FIG. 1 is a perspective view of the apparatus of the present invention for compressing a body limb.

Referring initially to FIG. 1, an apparatus for controlling an edema-relieving sleeve is shown, generally designated 10. As shown, the apparatus includes a hollow lightweight metal or plastic case 12 for holding the electro-pneumatic components and electrical components of the apparatus 10 which are disclosed below. Preferably, the case 12 has a top surface 14 and a display surface 16, and the display surface 16 extends downwardly away from the top surface 14 at an oblique angle. Further, a tubing surface 18 extends downwardly and inwardly away from the display surface 16.

As shown, a display window 20 is positioned on the display surface 16. The display window 20 can be any suitable display, such as a liquid crystal display, for displaying alpha-numeric characters and graphics. Additionally, a two-position on–off switch 22 is mounted on the display surface 16 for selectively energizing and deenergizing the electrical components of the apparatus 10. Moreover, a rotatable and depressible rotary encoder knob 24 is movably mounted on the display surface 16 for establishing an input means by which a person can enter information into the computer of the apparatus 10, as more fully disclosed below. Furthermore, a plurality of hollow, hard plastic or rubber fluid lines 26 extend outwardly from the tubing surface 18. In the presently preferred embodiment, up to fourteen (14) fluid lines 26 extend outwardly from the tubing surface 18.

Figure 2:
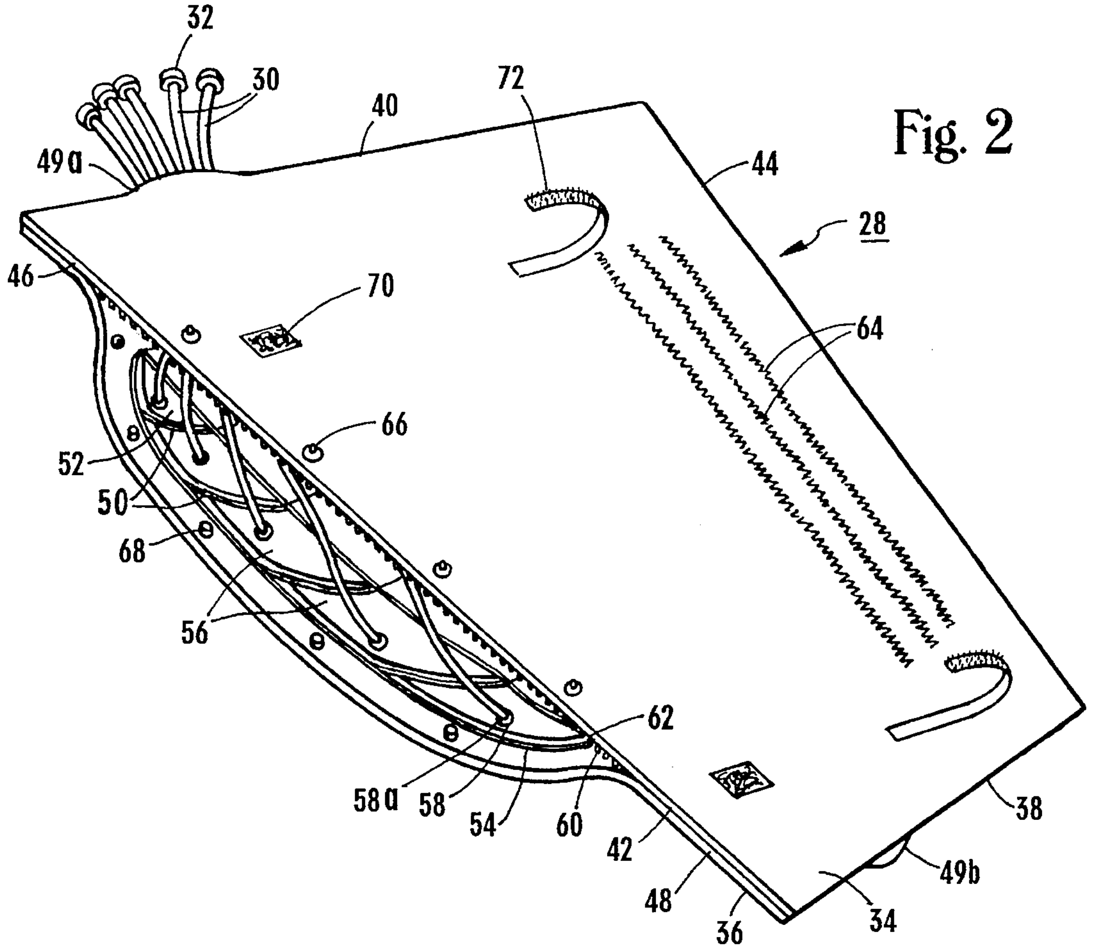
FIG. 2 is a perspective view of a leg sleeve of the present invention.

FIG. 2 shows an edema-relieving sleeve of the present invention, generally designated 28. The sleeve 28 shown in FIG. 2 is intended to be wrapped around a leg of patient to compress the leg and thereby alleviate swelling in the leg which can be caused by, e.g., lymphedema. Accordingly, the sleeve 28 is generally trapezoidal-shaped. It is to be understood, however, that the sleeve 28 can also be used to compress a patient's arm.

As shown in FIG. 2, the sleeve 28 includes a plurality of hollow, hard plastic or rubber fluid lines 30. Each fluid line 30 includes a fitting 32 for engaging a respective one of the fluid lines 26 shown in FIG. 1.

As further shown in FIG. 2, the sleeve 28 is formed with a first layer 34 and second layer 36, and each layer 34, 36 is preferably made of rugged, flexible, inelastic nylon or other suitable material. If desired, the second layer 36 can be made of relatively porous material, and one of the fluid lines 30 can be disposed between the layer and be perforated. Then, air can be directed through the fluid line 30 and out of the perforations between the layers 34, 36 to cool the patient's limb. If desired, the computer described below can regulate the flow of air between the layers 34, 36 of the sleeve 28.

The layers 34, 36 are positioned flushly together, and each layer 34, 36 is formed with a distal end, a proximal end, and first and second sides extending longitudinally between the ends to respectively establish a distal end 38 of the sleeve 28, a proximal end 40 of the sleeve 28, and first and second sides 42, 44 of the sleeve 28. As can be appreciated in reference to FIG. 2, the layers 34, 36 are sewn together on each side at proximal and distal sewn sections 46, 48. Also, the layers 34, 36 establish an aperture 49*a* in the proximal end 40 of the sleeve 28, and the fluid lines 30 extend through the aperture 49*a*. When the sleeve 28 is a leg sleeve, a second aperture 49*b* is established in the distal end 38 of the sleeve 28.

FIG. 2 shows that a plurality of hollow, flexible, inelastic nylon cell pockets 50 extend transversely between the layers 34, 36 from side to side of the sleeve 28 to establish a plurality of flexible cells 52. As shown, one transverse edge of each cell pocket 50 is sewn to the second layer 36, while the opposite edge of the cell pocket 50 is sewn to its immediately distal cell pocket 50. Consequently, the skilled artisan will recognize that each cell 52 overlaps its immediately adjacent neighboring cells 52. In the presently preferred embodiment, the sleeve 28 is formed with eleven (11) cells 52, although the particular number of cells can vary depending on the application of the sleeve 28. For example, a sleeve (not shown) can be configured as a waist garment and have fewer than eleven (11) cells.

In accordance with the present invention, each cell 52 has respective first and second ends (only first ends 54 are shown in FIG. 2) which are juxtaposed with the first and second sides 42, 44, respectively, of the layers 34, 36 of the sleeve 28. It is to be understood that the second ends of the cells 52 are identical in appearance and configuration as the first ends 54. Importantly, each first end 54 and each second end is open.

Still referring to FIG. 2, a plurality of flexible hollow inelastic inflatable bladders 56 are positioned in a respective cell 52. Each bladder 56 is formed with a respective hole 58 including an associated connector fitting 58*a*, and a respective one of the fluid lines 30 is engaged with each connector fitting 58*a* such that the fluid line 30 is in fluid communication with its associated bladder 56.

It may now be appreciated that because both ends of each cell 52 are open, replacement of the associated bladder 56 with another like bladder is facilitated. It may be further appreciated that the connector fittings 58*a* are disposed between the layers 34, 36 of the sleeve 28, and that consequently, the fluid lines 30 extend between the layers 34, 36 of the sleeve 28 and out of the aperture 49. Thus, the connection between each fluid line 30 and its associated bladder 56 is positioned within the sleeve 28, to prohibit inadvertent disconnection of the fluid line 30 from its bladder 56.

FIG. 2 shows that a first fastener strip 60 is positioned along a side 62 of the first layer 34. Preferably, the first fastener strip 60 is a zipper strip, and is sewn to the first layer 34. Additionally, a plurality of, preferably three (3), second fastener strips 64 are positioned side-by-side longitudinally on the sleeve 28, and the second fastener strips 64 are generally opposed to the first fastener strip 60. It is to be understood that each second fastener strip 64 is selectively engageable with the first fastener strip 60 as appropriate for the size of the limb around which the sleeve 28 is disposed to hold the sleeve 28 in place on the patient's leg.

If desired, a plurality of longitudinally-spaced top snap receivers 66 can be attached to the first layer 34, and a plurality of complementarily-shaped bottom snaps 68 can be attached to the second layer 36 to selectively engage the top snap receivers 66 and thereby selectively hold the sides of the layers 34, 36 together. Moreover, a plurality of first Velcro® fasteners 70 can be attached to the first layer 34 and a corresponding plurality of second Velcro® fasteners 72 which are complementary to the first Velcro® fasteners 70 can also be attached to the first layer 34. It is to be understood that when the sleeve 28 is wrapped around a patient's leg with the second layer 36 facing the leg, the first Velcro® fasteners 70 are engaged with the second Velcro® fasteners 72 to cover the ends of the first and second fastener strips 60, 64 when the strips 60, 64 are engaged with each other.

Figure 3:
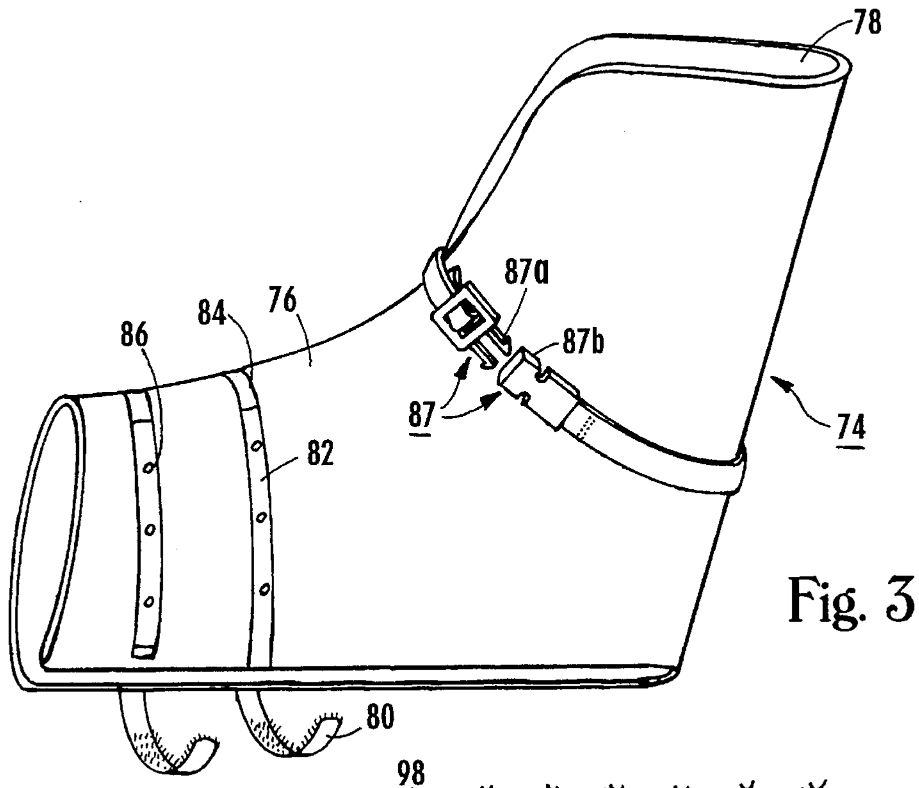
FIG. 3 is a perspective view of a foot sleeve of the present invention.

Now referring to FIG. 3, a foot sleeve is shown, generally designated 74. As shown, the foot sleeve 74 includes a surface 76 which defines an open toe end 78. It is to be understood that, like the sleeve 28 shown in FIG. 2, the foot sleeve 74 also includes one or more cells and inflatable bladders. In the presently preferred embodiment, the foot sleeve 74 includes a single cell and bladder. Thus, the foot sleeve 74 can be used for compressing the foot of a patient.

As shown in FIG. 3, a plurality of first fastening strips 80 are attached to the surface 76 of the foot sleeve 74, and a plurality of second fastening strips 82 which are configured for engaging the first fastening strips 80 are also attached to the surface 76. Preferably, the fastening strips 80, 82 are Velcro®.

As intended by the present invention, each second fastening strip 82 is removably attached to the surface 76 for permitting easy replacement of the second fastening strip 82 with another like strip without tearing or cutting the surface 76. In the presently preferred embodiment, a plurality of holder strips 84 are sewn to the surface 76 of the foot sleeve 74, and one or more snap receivers are mounted on each holder strip 84. Also, a plurality of snaps 86 are mounted on each second fastener strip 82, and the snaps 86 can be engaged with the snap receivers of the associated holder strip 84 to removably hold the second fastener strip 82 onto the holder strip 84.

If desired, a plurality of conventional buckle fasteners, generally designated 87 (only one buckle fastener 87 shown in FIG. 3) may be provided to further hold the sleeve 74 onto the foot of the patient. Each buckle fastener 87 has a snap element 87*a* and a receiving element 87*b* for releasably receiving the snap element 87*a* therein.

Figure 4:
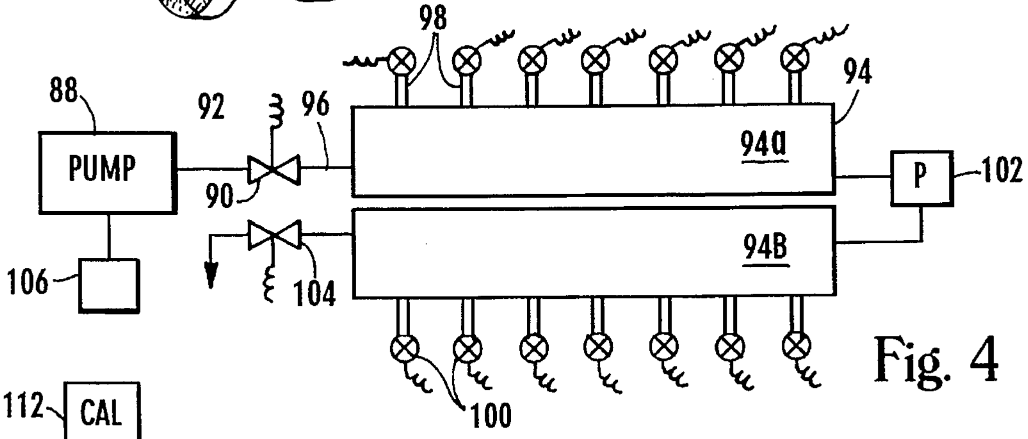
FIG. 4 is a schematic diagram showing the electro-pneumatic components of the present invention.

FIG. 4 schematically shows the electro-pneumatic components of the present invention. As shown, the apparatus 10 includes a source 88 of fluid pressure. In the presently preferred embodiment, the source 88 is a floating piston pump made by Medo of Japan. Preferably, the motor of the source 88 includes two windings, one for operating the source 88 using a one hundred ten volt (110 V) power input and one for operating the source 88 using a two hundred twenty volt (220 V) power input.

The source 88 of pressure is in turn connected to a normally shut solenoid-operated fill valve 90 via a fluid line 92, and the fill valve 90 is connected to a valve manifold 94 via a fluid line 96. In one embodiment, the valve manifold 94 includes first and second halves 94*a*, 94*b*, and is made by MAC Corp.

As shown in FIG. 4, a plurality of independently controllable normally open solenoid-operated bladder valves 98 are in fluid communication with the valve manifold 94. More specifically, seven (7) bladder valves 98 are bolted to the first half 94*a* of the manifold 94, and seven (7) bladder valves 98 are bolted to the second half 94*b* of the manifold 94. In accordance with the present invention, each bladder valve 98 is connectable to one of the fluid lines 26 shown in FIG. 1 and associated fluid line 30 shown in FIG. 2. Stated differently, the fluid lines 26, 30 and associated bladder valves 98 establish fluid pathways between the valve manifold 94 and the bladders 56.

It is to be understood that in sleeve embodiments having less than fourteen (14) bladders, a corresponding number of bladder valves 98 will be used during compression therapy, with the remaining unused bladder valves 98 staying shut, i.e., inactive. Thus, the present invention envisions the use of one bladder valve 98 per sleeve bladder.

Each bladder valve 98 includes a respective solenoid 100. Electrical power to each solenoid 100 can be selectively controlled to cause the solenoid 100 to open or shut the associated bladder valve 98. As more fully disclosed below, the solenoid 100 of each bladder valve 98 can be controlled by a computer independently of the other solenoids 100.

Hence, each bladder valve 98 can be placed in fluid communication with a respective one of the bladders 56 shown in FIG. 2. Also, each bladder valve 98 is controllable independently of the other valves 98. Thus, each bladder valve 98 can be individually controlled to dynamically establish a sequence of filling the bladders 56, to dynamically establish the pressure within each bladder 56 independently of the pressures in the other bladders 56, and to perform other functions, such as measuring the pressure within each bladder 56, independently of the other bladders 56.

As further shown in FIG. 4, a high-accuracy pressure transducer 102 is in fluid communication with the manifold 94. The pressure transducer 102 can be any suitable high-accuracy instrument, e.g., a type SCX05DN transducer, for generating an electrical signal in response to the pressure within the manifold 94. The skilled artisan will recognize that the pressure transducer 102 can be caused to generate an electrical signal representative of the fluid pressure within any one or more of the bladders 56 by opening the bladder valve or valves 98 associated with the bladder or bladders 56 sought to be monitored and closing the valves 98 associated with the remaining bladders 56.

A normally open solenoid-operated exhaust valve 104 is in fluid communication with the manifold 94. The exhaust valve 104 can be controlled to selectively exhaust the manifold 94 and thus to depressurize any one or more of the bladders 56. In the presently preferred embodiment, the fill valve 90, bladder valves 98, and exhaust valve 104 are solenoid valves made by MAC Corp.

FIG. 4 also shows that a solid state power switch 106 is electrically connected to the source 88 of pressure. The power switch 106 is controllable to selectively energize the source 88 and thereby pressurize the valve manifold 94.

Figure 5:
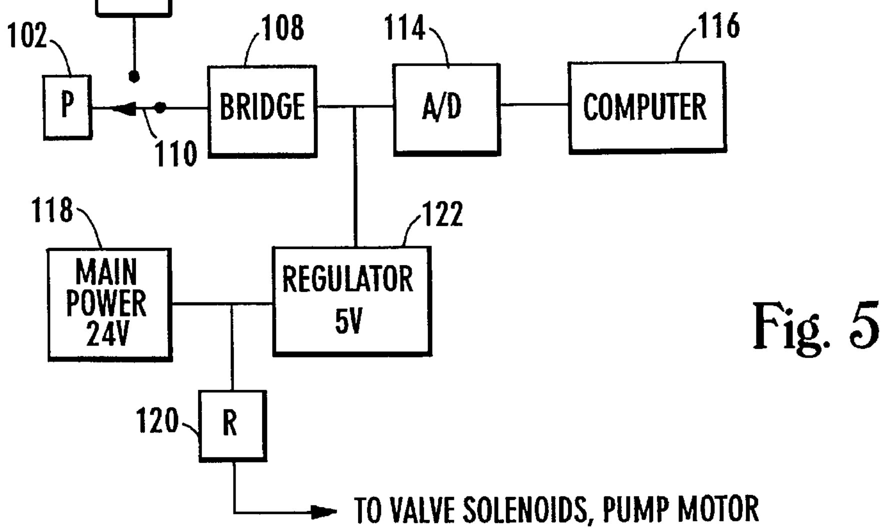
FIG. 5 is a schematic diagram showing the electrical components associated with the pressure sensor.

Now referring to FIG. 5, the pressure transducer 102 is electrically connected to a bridge signal conditioner 108 via a switch 110. The switch 110 can be operated to connect the signal conditioner 108 to a conventional precision resistance network calibration circuit 112 to monitor the calibration of the electronic circuitry shown in FIG. 5.

As intended by the present invention, the bridge signal conditioner 108 conditions and amplifies the electrical signal that is generated by the pressure transducer 102. In one presently preferred embodiment, the conditioner 108 includes a type LT1014DN amplifier having three operational amplifiers that amplify the gain of the signal from the pressure transducer 102 by about one hundred eighty six (186).

As shown in FIG. 5, the signal from the conditioner 108 is sent to an analog-to-digital (A/D) converter 114. In the embodiment shown in FIG. 5, the A/D converter 114 is twelve (12) bit a type MAX191 converter.

A computer 116 receives the digitized pressure signal from the A/D converter 114 for processing as more fully disclosed below. If desired, a blood pressure measuring sensor can be disposed in the sleeve 28 and electrically connected to the computer 116 for adjusting or stopping treatment of the patient in response to the blood pressure and/or pulse of the patient, and for displaying the blood pressure/pulse on the display 20 (FIG. 1).

Preferably, the computer 116 includes a type 80C31 microcomputer chip. In addition to the functions of the computer 116 discussed below, the computer 116 will reset to zero the pressure signal from the transducer 102 whenever the source 88 of pressure has been inactivated for longer than one hour. Such resetting improves the accuracy of the apparatus 10 in precisely pressurizing the bladders 56 to their programmed pressures.

FIG. 5 also shows that a twenty four (24) volt direct current (dc) main power supply 118 is provided, and the main power supply 118 is electrically connected to the valve solenoids 100 and source 88 of fluid pressure through a resistor network 120 for energizing the solenoids 100 and source 88. In accordance with the present invention, the voltage drop across the resistor network 120 can be measured to determine the magnitude of the dc current through the resistor 120. A high or low magnitude of the dc current may be representative of an abnormal condition, e.g., a failed solenoid 100. In the presently preferred embodiment, the magnitude of the dc current is monitored several times each second by the computer 116. Also, current flow through the electronic components described herein can be monitored at predetermined intervals for monitoring component and sensor performance.

A type LM7805CKCA voltage regulator 122 is connected to the main power supply 118 for generating an output voltage of five (5) volts. The output voltage of the regulator 122 is sent to the electronic components as shown to energize the electronic components.

Figure 6:
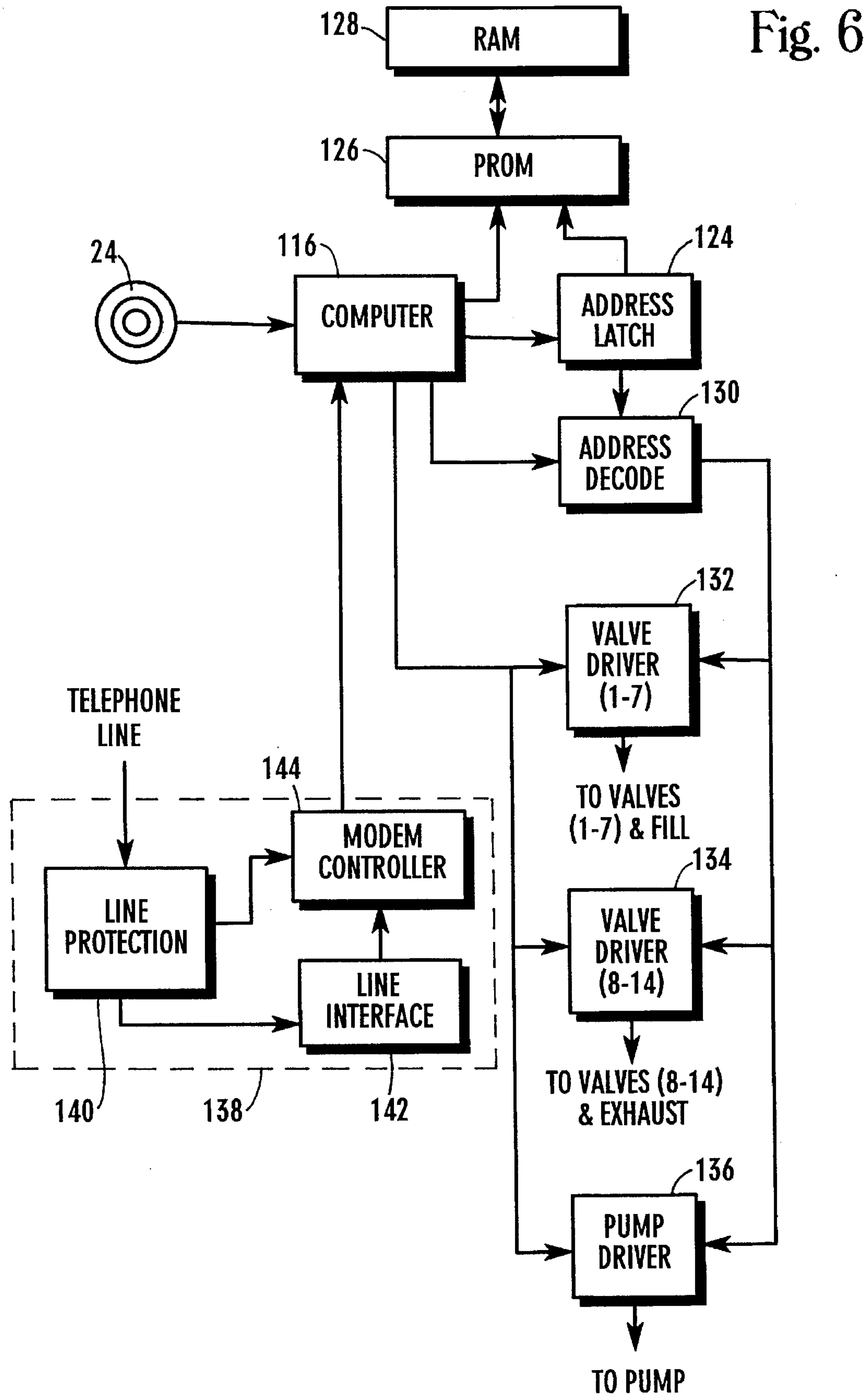
FIG. 6 is a schematic diagram showing the electrical control components of the present invention.

Now referring to FIG. 6, the rotary encoder knob 24 is electrically connected to the computer 116. Also, the computer 116 is electrically connected to a type 74HC573 address latch 124, and both the latch 124 and computer 116 are connected to a type 29C010 "flash" programmable read-only memory (PROM) 126. Alternatively, the PROM 126 can be an ultraviolet (UV) PROM or other programmable chip. The PROM 126 in turn is connected to a battery-backed type DS1386 thirty two kilobit (32K) random access memory (RAM) and real time clock (RTC) chip 128. Both the computer 116 and address latch 124 are also connected to a type 74HC138 address decoder 130.

As intended by the present invention, predetermined pumping sequence programs can be stored in the memory circuitry described above. Also, a user of the apparatus 10 can enter program data into the computer 116 by appropriately manipulating the rotary encoder knob 24 to create operator-defined programs which are tailored to particular patients. These programs are also stored in the circuitry described above. Further, the memory circuitry described above can store treatment history parameters, including time and date of last treatment, average treatment time duration, average maximum treatment pressure, and the number of treatments performed in immediately preceding periods, e.g., the last thirty, sixty, and ninety days.

The computer 116 controls the operation of the source 88 of pressure and the valves 90, 98, 104 shown in FIG. 4 in response to program commands stored in the memory circuitry described above. Accordingly, the computer 116 is electrically connected to first and second type TPIC6273N valve drivers 132, 134 and to a type TPIC6273N pump driver 136. Also, the address latch 124, through the address decoder 130, is electrically connected to the drivers 132, 134, 136 to generate signals representative of which particular solenoid 100/pump motor is to receive the commands from the computer 116.

As the skilled artisan will appreciate, the first valve driver 132 is an electronic chip which functions as an interface between the computer 116 and the valve solenoids 100 of the first seven bladder valves 98 to control the first seven solenoids 100. The first valve driver 132 also controls the solenoid of the fill valve 90. Also, the second valve driver 134 is an electronic chip which functions as an interface between the computer 116 and the solenoids 100 of the second seven bladder valves 98 to control the solenoids 100. The second valve driver 134 also controls the solenoid of the exhaust valve 104. Further, the pump driver 136 functions as an interface between the computer 116 and the motor of the source 88 of fluid pressure.

As additionally shown in FIG. 6, a modem 138 can be connected to the computer 116 for establishing a means by which a user remote from the apparatus 10 can nevertheless program and otherwise operate and control the apparatus 10. Furthermore, patient data stored in the apparatus 10 can be transmitted over the modem 138 to a remote location.

As shown in FIG. 6, the modem 138 includes conventional modem circuitry, including a line protector 140. The line protector 140 includes an isolation transformer and wave protection diode circuitry, in addition to a type 4N35 movistor. Moreover, the modem 138 includes a type 73M376 line interface chip 142 and a type 73K324L modem controller chip 144.

Figure 7:
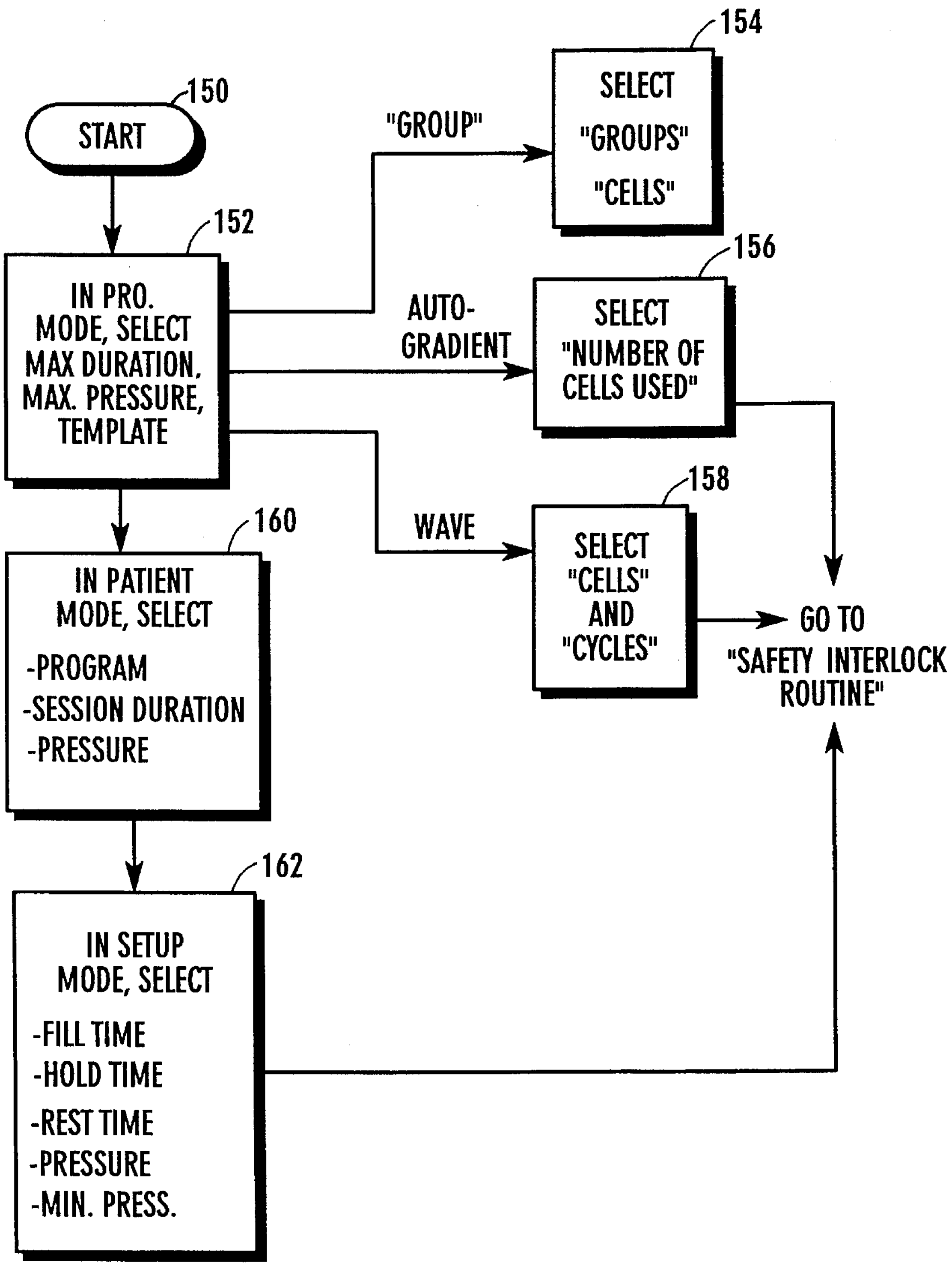
FIG. 7 is a flow chart showing some the parameter selection steps of the present invention.

Now referring to FIG. 7, all program inputs to the computer 116 (and, thus, all treatment parameters) can be entered by appropriately manipulating the encoder 24 (FIG. 1), starting at block 150. As block 152, the operator may select a "professional" mode. In the presently preferred embodiment, the professional mode can be entered only upon entering a password. Consequently, an untrained patient is prevented from entering the professional mode, and only a trained operator possessing the password can enter the professional mode.

In the professional mode, the following parameters may be defined: maximum session duration, maximum allowed system pressure, and template program. Available treatment templates include "group", "wave", "autogradient", and "user-defined". In selecting a particular treatment template, the operator selects a predetermined treatment profile, except when the operator selects "user-defined", in which case the operator creates a treatment profile subject to the limitations of the interlock features discussed below.

If the group template is selected, at block 154 the operator enters the number of groups to be used and the number of cells 52 which are to be simultaneously pressurized to thereby establish each group. Accordingly, it may be appreciated that in the group mode, groups of bladders 56, each of which group includes the preselected number of adjacent cells to be simultaneously pressurized, are filled from the source 88 of pressure.

In the autogradient program, the bladders 56 of the sleeve 28 are filled in sequence from the distal-most bladder 56 to the proximal-most bladder 56 at fill times and pressures for each bladder 56 which can be collectively or individually programmed as disclosed below.

Accordingly, at block 156, if autogradient has been selected the operator enters the desired number of cells 52 to be used. If the desired number is less than the total number of cells 52 available, a predetermined interlock which is programmed into the computer 116 prevents the proximal-most cells 52 from being used. Thus, for the sleeve 28, if ten cells are selected, the ten distal-most bladders 56 will be pressurized. Consequently, it is to be appreciated that the above-described safety interlock prevents pressurizing a bladder 56 that is located proximal to an unpressurized bladder 56, which would otherwise result in fluid being deleteriously urged toward the extremity being treated and not toward the trunk of the body as is desired in treating edema.

On the other hand, the operator could select the "wave" program at block 152, and move to block 158 to define the wave program parameters of "number of cells 52 per wave" and "number of cycles for each wave". Thus, in the wave program, each wave consists of a predetermined number of cells 52, and the cells 52 in the first wave are pressurized and depressurized a predetermined number of times (cycles) before the cells 52 in the second wave are pressurized. The second wave may include cells 52 that were also in the first wave, in addition to cells 52 that were not in the first wave. Importantly, as a safety interlock, the computer 116 ensures that no cells 52 of a current wave are distal to any cells 52 of a preceding wave which are to remain unpressurized during the current wave.

At block 160 the operator may enter the "patient" mode, without requiring knowledge of a password. Thus, an untrained patient, in addition to trained technicians, can enter the patient mode to enter the following treatment parameters: select program, session duration, and maximum pressure to be used during the session. Importantly, the computer 116 prevents entering a session duration or maximum pressure in the patient mode which exceed the maximum duration and maximum pressure, respectively, entered in the professional mode.

At block 162, an operator possessing the appropriate password may enter the "setup" mode to define the following parameters: "minimum fill time" period for filling all bladders 56 to be filled, "hold time" period for maintaining the desired pressure within the bladders 56, "rest time" period during which pressure in the bladders 56 is maintained at a computer 166—determined exhaust pressure between fill cycles, "maximum pressure" to which the distal-most bladder 56 can be pressurized, and the "minimum pressure" to which the proximal-most bladder 56 that is to be used will be pressurized. From blocks 158, 160, 162 the computer proceeds to the safety interlock routine shown in FIG. 8. It will be understood that any treatment program can be stored in electronic memory of the apparatus 10.

Figure 8:
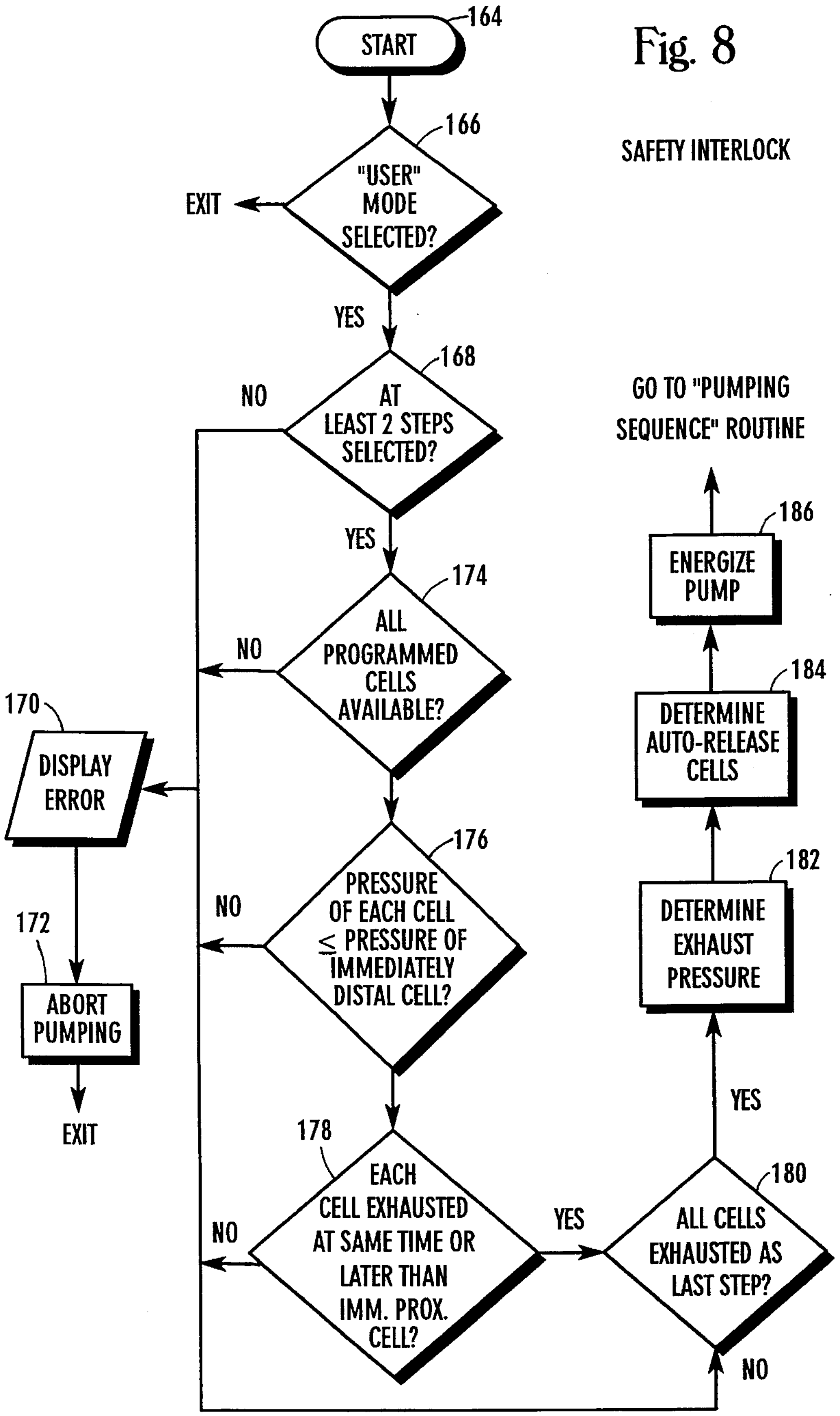
FIG. 8 is a flow chart showing the interlock features of the present invention.

Now referring to FIG. 8, the computer 116 conducts a plurality of safety and validity interlock checks of the treatment parameters entered by the operator of the apparatus 10. The computer starts at block 164 and proceeds to decision block 166, wherein it is determined whether a user mode program had been selected. If not, the computer 116 exits the routine. Otherwise, the computer 116 proceeds to decision block 168 to determined whether at least two program steps have been defined. If not, the computer 116 proceeds to output block 170 to display an error warning on the display 20 (FIG. 1), and then the computer 116 prevents energization of the source 88 of pressure at block 172 and exits. Otherwise, the computer 116 proceeds to decision block 174.

At decision block 174, the computer 116 determines whether all cells 52 which had been programmed are available in the particular compression sleeve to be used. For example, the pressure sensor 102 (FIG. 4) may sense that one or more bladders 56 have leaks, and the computer 116 accordingly determines that the leaking bladders 56 are unavailable for use. If all programmed cells 52 are not available, the computer 116 proceeds to output block 170.

Otherwise, the computer 116 proceeds to decision block 176, wherein the computer 116 determines whether the programmed pressure of any bladder 56 associated with a cell 52 is less than or equal to the programmed pressure in the immediately distal bladder 56, to avoid deleteriously urging fluid toward the extremity being treated and not toward the trunk of the patient's body as desired. If the test is negative, the computer 116 moves to output block 170. Otherwise, if the programmed pressure of each bladder 56 is less than or equal to the programmed pressure in the immediately distal bladder 56, the computer 116 proceeds to decision block 178.

At decision block 178, the computer 116 determines whether each cell bladder 56 is exhausted at the same time or later than the immediately proximal bladder 56 is exhausted. If not, the computer 116 moves to output block 170. Otherwise, the computer 116 moves to decision block 180, wherein the computer 116 determines whether, as a last step, all cell bladders 56 are programmed to be exhausted. If not, the computer 116 moves to output block 170.

On the other hand, if all cell bladders 56 have been programmed to be exhausted, the computer 116 moves to block 182 to determine exhaust pressure. At block 182, the computer 116 defines exhaust pressure to be the lower of: minimum cell pressure minus thirty millimeters of Mercury (30 mm Hg) or fifty millimeters of Mercury (50 mm Hg). In no case will exhaust pressure be less than twenty millimeters of Mercury (20 mm Hg). Thus, it is to be understood that the bladders 56 are pressurized slightly above atmospheric pressure, even during exhaust sequences. Consequently, the bladders 56 may be more quickly pressurized to their fill pressure for the succeeding fill sequence.

Next, the computer 116 moves to block 184 to determine which cells 52 will be defined as "auto-release" cells. The auto-release cells are determined to be the fewer of the first three cells 52 used in the particular treatment program or the total number of cells used minus one. Auto-release are cells 52 that contain bladders 56 which are to be automatically exhausted upon the occurrence of a predetermined condition, e.g., the exceeding of the hold time defined above. From block 184, the computer 116 moves to block 186 to energize the source 88 of pressure and exit to the pumping sequence routines described below.

Figure 9:
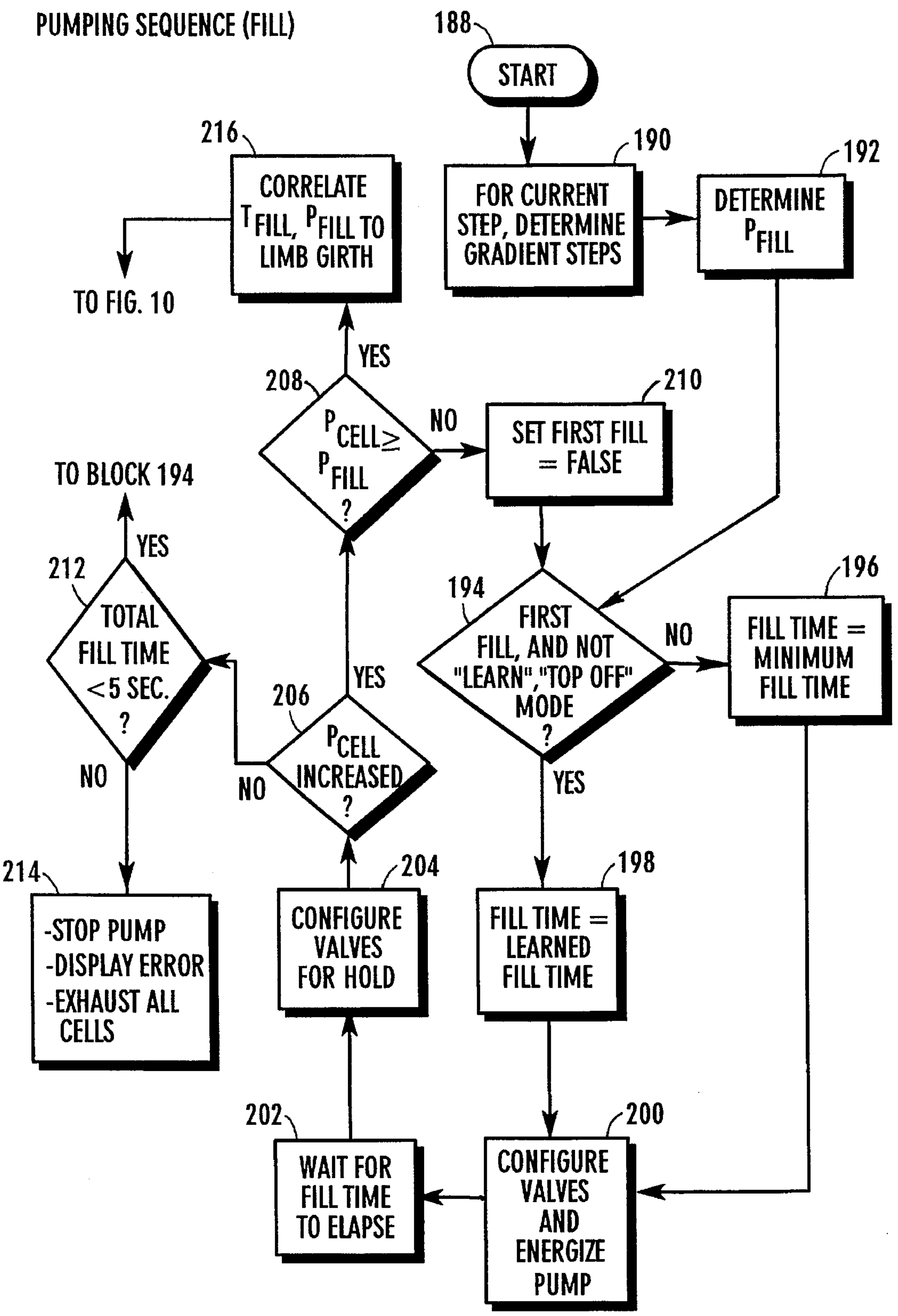
FIG. 9 is a flow chart showing the operational steps of the fill portion of the pumping sequence.

Now referring to FIG. 9, the computer 116 begins the pumping sequence at block 188 and moves to block 190, wherein the computer 116 determines the number of gradient steps, i.e., the number of pumping cycles required to fill the cells 52 which are to be filled during the current cycle. Typically, unless a prolonged fill time was programmed by the operator of the apparatus 10, the number of gradient steps will be one (1). Otherwise, the number of gradient steps is determined by dividing the predefined fill time by the required change in pressure.

Next, at block 192, the computer 116 determines a fill pressure, i.e., the pressure to which the bladder or bladders 56 of the current cycle are to be filled. The computer 116 determines the fill pressure to be the programmed pressure, times a factor "F" divided by the number of gradient steps determined at block 190. In turn, the factor "F" is determined to be 100%—the number of bladders 56 remaining to be filled.

Accordingly, it may now be appreciated that by initially filling the bladders 56 being filled in the current cycle to a pressure that is somewhat less than their programmed pressure, pressure increases in the bladders 56 which are caused by subsequent pressurizations of other bladders 56 which overlap the bladder or bladders 56 being currently filled are accounted for. Stated differently, unintentional overpressurization of any particular bladder 56 caused by other pressurized bladders 56 that overlap the particular bladder 56 is avoided by filling each bladder 56 to a pressure which is marginally less than its programmed pressure.

From block 192, the computer 116 proceeds to decision block 194, wherein the computer 116 determines whether the current cycle iteration is the first fill iteration of the current cycle, or whether the current iteration is the second fill iteration of the current cycle, or whether the current iteration is a "top off mode" iteration. If the test at block 196 is negative, the computer 116 moves to block 196, and sets the fill time equal to a minimum fill time, preferably set to a value of fifty milliseconds (50 ms).

Otherwise, the computer 116 moves to block 198 to set the fill time equal to the "learned" fill time, which is defined as either a default value (for the first iteration) or the total time elapsed filling during the first and second iterations (for the second and subsequent iterations).

From block 196 or block 198, as appropriate, the computer 116 moves to block 200 to open the fill valve 90 (FIG. 4), shut the exhaust valve 104, shut the bladder valves 98 associated with the bladders 56 not being pressurized, and open the bladder valve or valves 56 associated with the bladder or bladders 56 being pressurized in the current fill cycle. It may now be appreciated that in configuring the valves 90, 98, 104, the computer 116 sends a signal through the appropriate valve drivers 132, 134 (FIG. 6) to energize the associated valve solenoids 100. Preferably, the computer 116 waits for a few hundred milliseconds (e.g., two hundred milliseconds) after a valve operation before validating a pressure signal from the transducer 102, to thereby allow pressure within the apparatus 10 to stabilize.

Also at block 200, the computer 116 energizes the source 88 of pressure (for the first pressurizing sequence) by sending a signal to the pump driver 136 (FIG. 6). Ordinarily, once energized, the source 88 of pressure remains activated throughout a therapy session, with the therapy being controlled by opening and shutting the valves 90, 98, 104 as described below.

Next, at block 202, the computer 116 waits for the computer fill time to elapse, and then shuts the fill valve 90 to isolate the bladders 56 and thereby hold the bladders 56 at pressure for the predefined hold time at block 204. Then, at decision block 206, the computer 116 determines whether the pressure in the bladders 56 being filled has increased. If so, the computer 116 proceeds to decision block 208 to determine whether the pressure within the bladder or bladders 56 being filled is greater to or equal than the calculated fill pressure. If not, the computer 116 moves to block 210 to set the "first fill" flag to FALSE, and then to decision block 194.

If, at decision block 206, the computer 116 determined that pressure in the bladder or bladders 56 being filled has not increased, the computer 116 proceeds to decision block 212 to determine whether the total fill time elapsed is less than five (5) seconds. If so, the computer 116 proceeds to block 194. Otherwise, the computer proceeds to block 214 to deenergize the source 88 of pressure, display an error message on the display 20, and exhaust all bladders 56. Thus, blocks 206, 212, and 214 essentially establish a tester for determining the fluid integrity of each bladder 56 in response to the pressure signal.

If, at decision block 208, the computer 116 determined that the pressure in the bladder 56 being filled equals or exceeds the fill pressure, then the computer 116 proceeds to block 216 to correlate the time of fill and/or actual fill pressure to a limb girth. As recognized by the present invention, the actual fill time required to pressurize a bladder 56 to a predetermined pressure decreases with increasing limb girth. Also, for a given fill time, the pressure to which a bladder 56 is pressurized increases with increasing limb girth.

Accordingly, the computer 116 can correlate actual fill time, or pressure, or both, by accessing a table or by calculating limb girth based upon an empirically determined equation. The limb girth is then stored or transmitted via the modem 138 (FIG. 6) to medical personnel for further analysis. If desired, measured limb girth can be compared to a baseline girth entered by an operator or determined by the computer 116.

It is accordingly to be understood that the computer 116 can access the RAM/RTC 128 (FIG. 6) timer for measuring the time period for filling at least one bladder 56 and generating a timing signal in response thereto. It is to be further understood that each bladder 56 defines an annular ring when the sleeve 56 is operably engaged with a limb, and that block 216 establishes a determiner for determining the radius of at least one of the rings based on the timing signal. From block 216, the computer proceeds to the process shown in FIG. 10.

Figure 10:
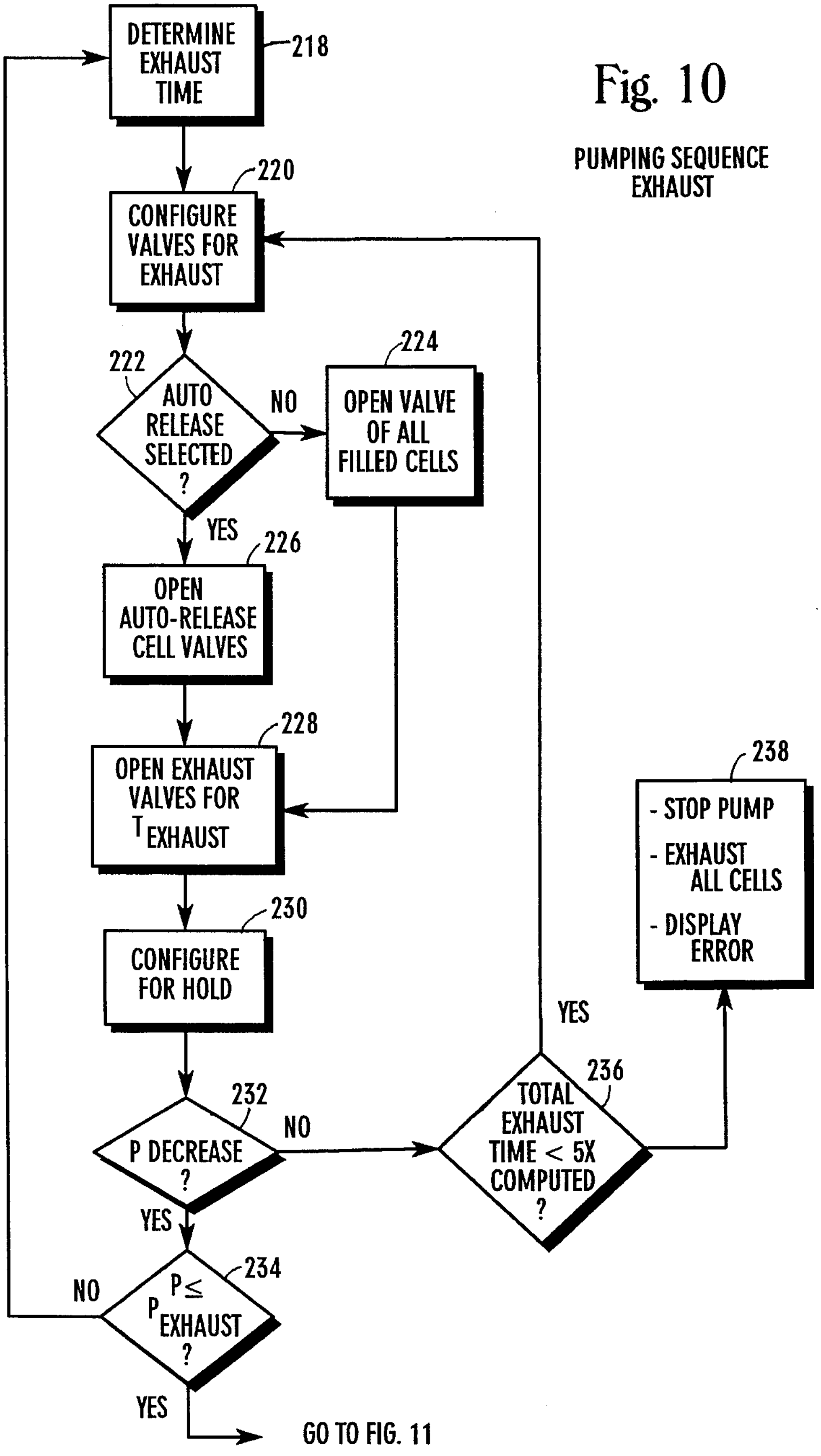
FIG. 10 is a flow chart showing the operational steps of the exhaust portion of the pumping sequence.

Now referring to FIG. 10, the exhaust sequence of the computer 116 can be seen. At block 218, the computer 116 determines the time period during which the bladder valves 98 will be held open to exhaust the bladders 56. Exhaust time is calculated as the lesser of one second or the product of the following three factors: the difference between current pressure and exhaust pressure, one-half of the number of bladders 56 to be exhausted, and ten milliseconds (10 ms).

Next, at block 220, the computer 116 configures the valves of the system for exhaust. To do so, the computer moves to decision block 222 to determine whether automatic release has been selected. If so, the computer moves to block 226 to open the bladder valves 98 associated with the auto-release bladders 56. Otherwise, the computer 116 moves to block 224 to open the bladder valves 98 which are associated with all of the bladders 56 to be exhausted.

From block 226 or 224, the computer 116 moves to block 228 to open the exhaust valve 104 and hold the valve 104 open for the predefined exhaust time period. Then, the computer 116 moves to block 230 to shut the exhaust valve 104.

Next, at decision block 232, the computer 116 determines whether the pressure in the bladders 56 being exhausted has decreased. If so, the computer 116 moves to decision block 234 to determine whether the pressure in the bladders 56 is less than or equal to the exhaust pressure. If not, the computer returns to block 218. Otherwise, the computer 116 proceeds to the sequence shown in FIG. 11.

If, on the other hand, if the computer 116 determines that the pressure in the bladders 56 being exhausted has not decreased at decision block 232, the computer 116 moves to decision block 236 to determine whether the total exhaust time is less than the time determined at block 218. If so, the computer 116 returns to block 220. Otherwise, the computer 116 proceeds to block 238 to deenergize the source 88 of pressure, display an error message on the display 20, and exhaust all bladders 56.

Figure 11:
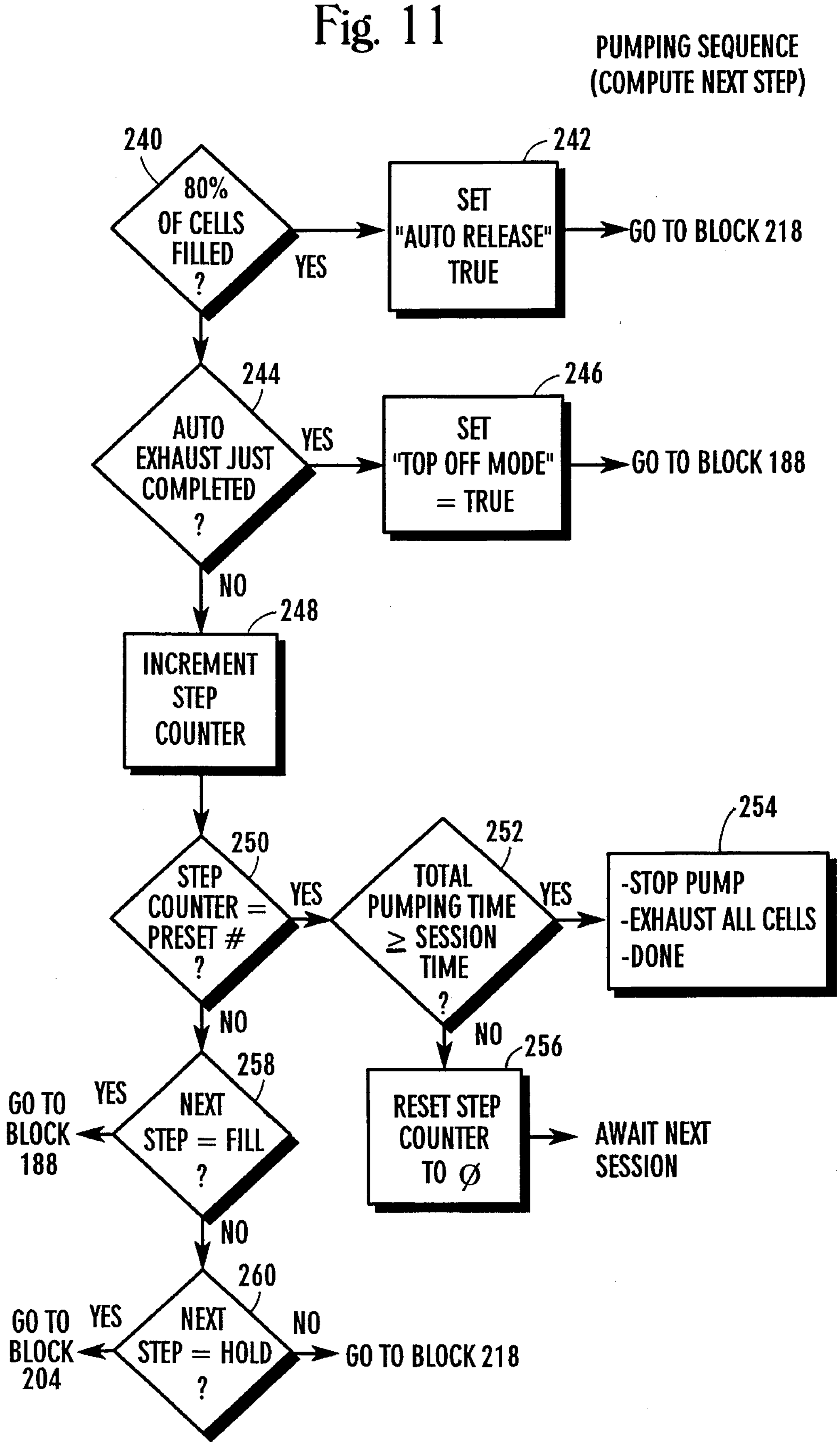
FIG. 11 is a flow chart showing the operational steps of the next step portion of the pumping sequence.

Now referring to FIG. 11, at decision block 240 the computer 116 determines whether eighty per cent (80%) of the bladders 56 have been pressurized. If so, the computer 116 moves to block 242 to define automatic release as being TRUE, and then the computer 116 proceeds to block 218 of FIG. 10. Otherwise, the computer 116 moves to decision block 244, wherein the computer 116 determines whether an automatic exhaust sequence has been completed. If so, the computer 116 moves to block 246 to define "top off" mode as being TRUE (i.e., to invoke the top off mode), and then the computer 116 returns to block 188 of FIG. 9.

On the other hand, if the test at decision block 244 was negative, the computer 116 moves to block 248 to increment a step counter by one (1), and then moves to decision block 250. At decision block 250, the computer 116 determines whether the counter equals the predetermined number of steps in the sequence. If so, the computer 116 moves to decision block 252 to determine whether the total session time equals or exceeds the programmed session time. If so, the computer 116 proceeds to block 254 to deenergize the source 88 of pressure and exhaust all bladders 56. Otherwise, the computer 116 proceeds to block 256 to reset the step counter to zero and await the next session.

If the test at decision block 250 was negative, the computer 116 proceeds to decision block 258 to determine whether the next step to be accomplished is a fill step. If so, the computer 116 proceeds to block 188 in FIG. 9. Otherwise, the computer 116 proceeds to decision block 260 to determine whether the next step is a hold step. If not, the computer 116 proceeds to block 218 in FIG. 10. Otherwise, the computer 116 proceeds to block 204 of FIG. 9.

The computer 116 can also include a pause feature that is invoked by appropriately manipulating the rotary encoder 24. The pause feature can be invoked to pause the treatment therapy to permit the patient to refresh himself as needed.

While the particular method and apparatus for applying pressure to a body limb as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. An apparatus for applying pressure to a patient's limb, comprising:

a source of pressure;

a sleeve surroundingly engageable with the limb, the sleeve including a plurality of individually inflatable bladders;

a plurality of electrically-operated bladder valves in fluid communication with the source of pressure, each bladder valve also being in fluid communication with a respective one of the bladders for selectively establishing a respective pathway for fluid communication between the source of pressure and the associated bladder;

a computer for individually controlling each valve to variably pressurize the bladders in a variable sequence; and a timer for measuring the time period for filling at least one bladder and generating a timing signal in response thereto, wherein each bladder defines an annular ring when the sleeve is operably engaged with a limb, and the computer includes a determiner for determining the radius of at least one of the rings based on the timing signal.

2. The apparatus of claim 1, further comprising:

a valve manifold in fluid communication with each of the bladder valves; and an electrically-operated fill valve in fluid communication with the source of pressure and the valve manifold for selectively establishing fluid communication between the source of pressure and the valve manifold.

3. The apparatus of claim 2, further comprising an electrically-operated exhaust valve in fluid communication with the valve manifold for selectively depressurizing the valve manifold.

4. The apparatus of claim 3, wherein the fill valve and the exhaust valve are controlled by the computer.

5. The apparatus of claim 4, further comprising a pressure sensor in fluid communication with the manifold for generating an electrical pressure signal representative of the pressure within the valve manifold, the pressure sensor being electrically connected to the computer for sending the pressure signal to the computer.

6. The apparatus of claim 5, wherein the computer includes a tester for determining the fluid integrity of each bladder in response to the pressure signal.

7. The apparatus of claim 6, wherein the computer includes an interlock for preventing pressurizing a bladder upon the occurrence of a predetermined condition.

8. The apparatus of claim 7, wherein the interlock prevents pressurizing a first bladder to a greater pressure than the pressure of a second bladder distal to the first.

9. The apparatus of claim 1, wherein the sleeve includes first and second layers, each layer being formed with a distal end, a proximal end, and first and second sides extending longitudinally between the ends, wherein the sleeve also includes a plurality of pockets extending transversely from side to side for holding the bladders, and wherein each pocket has respective first and second ends juxtaposed with the first and second sides, respectively, of the layers of the sleeve, both ends of each pocket being open to facilitate replacing the associated bladder with another bladder.

10. The apparatus of claim 9, further comprising a first fastener strip positioned along a first side of one of the layers and a plurality of second fastener strips positioned side-by-side longitudinally on the sleeve generally opposed to the first fastener strip, each second fastener strip being selectively engageable with the first fastener strip as appropriate for the size of the limb around which the sleeve is disposed.

11. The apparatus of claim 10, wherein one of the ends of the sleeve is formed with an aperture and each bladder is formed with an opening, and the apparatus further comprises:

a plurality of connector fittings disposed within the sleeve between the layers, each connector fitting being respectively engaged with one of the openings; and a plurality of fluid lines, each engaged with a respective one of the connector fittings and each fluid line extending out of the aperture of the sleeve.

12. The apparatus of claim 1, wherein the sleeve includes a layer having at least one first fastening strip and at least one second fastening strip configured for engaging the first fastening strip, wherein the second fastening strip is removably attached to the layer for permitting easy replacement of the second fastening strip with another like strip without tearing or cutting the layer.

13. An apparatus for inflating a sleeve having a plurality of inflatable bladders when the sleeve is surroundingly engaged with a body limb for compressing the limb, comprising:

a fluid pump;

a plurality of fluid pathways in fluid communication with the fluid pump, each fluid pathway connecting the fluid pump to a respective one of the bladders;

a plurality of valves, each disposed in a respective one of the fluid pathways for selectively establishing fluid communication from the fluid pump to the associated bladder, each valve being controllable independently of the other valves to dynamically establish a sequence of filling the bladders and to dynamically establish the pressure within each bladder independently of the pressures in the other bladders;

a computer; and a timer for measuring the time period for filling at least one bladder and generating a timing signal in response thereto, wherein each bladder defines an annular ring when the sleeve is operably engaged with a limb, and the computer includes a determiner for determining the radius of at least one of the rings based on the timing signal.

14. The apparatus of claim 13, wherein the valves are solenoid valves, and the device further comprises a plurality of valve controllers for controlling respective valves, the computer controlling the valve controllers.

15. The apparatus of claim 14, further comprising:

a valve manifold in fluid communication with each of the solenoid valves; and an electrically-operated fill valve in fluid communication with the fluid pump and the valve manifold for selectively establishing fluid communication between the pump and the valve manifold.

16. The apparatus of claim 15, further comprising an electrically-operated exhaust valve in fluid communication with the valve manifold for selectively depressurizing the valve manifold.

17. The apparatus of claim 16, wherein the fill valve and the exhaust valve are controlled by the computer.

18. The apparatus of claim 17, further comprising a pressure sensor in fluid communication with the manifold for generating an electrical pressure signal representative of the pressure within the valve manifold, the pressure sensor being electrically connected to the computer for sending the pressure signal to the computer.

19. The apparatus of claim 18, wherein the computer includes a tester for determining the fluid integrity of each bladder in response to the pressure signal.

20. The apparatus of claim 19, wherein the computer includes an interlock for preventing pressurizing a bladder upon the occurrence of a predetermined condition.

21. The apparatus of claim 20, wherein the interlock prevents pressurizing a first bladder to a greater pressure than the pressure of a second bladder distal to the first.

22. The apparatus of claim 21, wherein the computer includes an electronic memory for storing patient treatment parameters.

* * * * *